c

(12) United States Patent
Han et al.

(10) Patent No.: US 11,041,963 B2
(45) Date of Patent: Jun. 22, 2021

(54) RADIATION DOSE MEASUREMENT DEVICE AND MEASUREMENT METHOD

(71) Applicants: Research & Business Foundation Sungkyunkwan University, Suwon-si (KR); Samsung Life Public Welfare Foundation, Seoul (KR)

(72) Inventors: Young Yih Han, Seoul (KR); Won Joong Cheon, Bucheon-si (KR); Hyun Uk Jung, Seoul (KR); Moon Hee Lee, Seoul (KR); Sung Koo Cho, Seoul (KR)

(73) Assignees: Research & Business Foundation Sungkyunkwan University, Suwon-si (KR); SAMSUNG LIFE PUBLIC WELFARE FOUNDATION, Seoul (KR)

( * ) Notice: Subject to any disclaimer, the term of this patent is extended or adjusted under 35 U.S.C. 154(b) by 0 days.

(21) Appl. No.: 16/617,017

(22) PCT Filed: Apr. 6, 2018

(86) PCT No.: PCT/KR2018/004047
§ 371 (c)(1),
(2) Date: Nov. 26, 2019

(87) PCT Pub. No.: WO2018/216898
PCT Pub. Date: Nov. 29, 2018

(65) Prior Publication Data
US 2020/0088890 A1    Mar. 19, 2020

(30) Foreign Application Priority Data

May 26, 2017 (KR) .................. 10-2017-0065536

(51) Int. Cl.
*G01T 1/161* (2006.01)
*A61B 6/00* (2006.01)
*G01T 1/02* (2006.01)

(52) U.S. Cl.
CPC .............. *G01T 1/161* (2013.01); *A61B 6/542* (2013.01); *G01T 1/023* (2013.01)

(58) Field of Classification Search
CPC .. A61B 6/542; G01T 1/16; G01T 1/20; G01T 1/023; G01T 1/161
See application file for complete search history.

(56) References Cited

FOREIGN PATENT DOCUMENTS

JP    2007-50052 A    3/2007
JP    5837937 B2    12/2015
(Continued)

OTHER PUBLICATIONS

International Search Report dated Jul. 6, 2018 in counterpart International Patent Application No. PCT/KR2018/004047 (2 pages in English and 2 pages in Korean).

*Primary Examiner* — David P Porta
*Assistant Examiner* — Fani P Boosalis
(74) *Attorney, Agent, or Firm* — NSIP Law

(57) ABSTRACT

A device for measuring a radiation dose according to the present invention includes a radiation exposure unit which exposes radiation, a frame unit which supports the radiation exposure unit, a measurement housing unit which is mounted on the frame unit, a scintillation unit which is mounted on the measurement housing unit and emits light due to the radiation exposed by the radiation exposure unit, an image capturing unit which captures an image of the scintillation unit, and a dose measuring unit which measures, on the basis of the captured image obtained by the image capturing unit, a dose of radiation to which the scintillation unit is exposed.

14 Claims, 13 Drawing Sheets

(56) References Cited

FOREIGN PATENT DOCUMENTS

| | | |
|---|---|---|
| KR | 10-0750991 B1 | 8/2007 |
| KR | 10-0804809 B1 | 2/2008 |
| KR | 10-1203676 B1 | 11/2012 |
| KR | 10-2015-0116223 A | 10/2015 |
| WO | WO-2013061762 A1 * | 5/2013 ....... H01L 27/14601 |

* cited by examiner

RADIATION DOSE MEASUREMENT DEVICE AND MEASUREMENT METHOD

CROSS REFERENCE TO RELATED APPLICATIONS

This application is a U.S. National Stage Application of International Application No. PCT/KR2018/004047, filed on Apr. 6, 2018, which claims the benefit under 35 USC 119(a) and 365(b) of Korean Patent Application No. 10-2017-0065536, filed on May 26, 2017, in the Korean Intellectual Property Office, the entire disclosure of which is incorporated herein by reference for all purposes.

TECHNICAL FIELD

The present invention relates to a device and method for measuring a radiation dose, and more particularly, to a device and method for measuring a radiation dose capable of measuring an in vivo radiation dose or the like used during radiotherapy.

BACKGROUND ART

Generally, radiotherapy is a type of therapy for treating cancer by intensively exposing cancer tissues such as human internal organs to radiation. Radiotherapy is a therapy using a phenomenon in which, when cells are exposed to radiation, as the radiation acts on the DNA and cell membrane of the cells, the cells die through a process such as cell division or apoptosis.

However, when biological tissues of the human body or the like are exposed to radiation, not only cancer tissues but also normal tissues located around the cancer tissues are exposed to radiation, causing a disorder of the normal tissues. Thus, radiation dose optimization is necessary to minimize an influence of radiation on the normal tissues while treating the cancer tissues.

A conventional radiation dose measuring device has a problem that, since a configuration of the device for measuring an in vivo radiation dose or the like is complex and the volume and mass of the device are large, making it difficult to mount and control the device, and an image displayed on a scintillation unit is distorted, it is difficult to accurately analyze the in vivo radiation dose. Therefore, there is a need for improvement.

The related art of the present invention has been disclosed in Korean Patent Registration No. 10-0750991 (Date of Registration: Aug. 14, 2007, Title of Invention: phantom device for measuring radiation dose).

DISCLOSURE

Technical Problem

The present invention is directed to providing a device and method for measuring a radiation dose capable of accurately measuring a radiation dose by correcting an image of a scintillation unit without applying a reflective mirror or the like.

And reducing the volume and mass of the device so that manufacturing and mounting thereof are facilitated and picking up.

Technical Solution

One aspect of the present invention provides a radiation dose measuring device including: a radiation exposure unit which exposes radiation; a frame unit which supports the radiation exposure unit; a measurement housing unit which is mounted on the frame unit; a scintillation unit which is mounted on the measurement housing unit and emits light due to the radiation exposed by the radiation exposure unit; an image capturing unit which captures an image of the scintillation unit; and a dose measuring unit which measures, on the basis of the captured image obtained by the image capturing unit, a dose of radiation to which the scintillation unit is exposed.

The measurement housing unit may include a measurement housing on which the scintillation unit and the image capturing unit are mounted and a housing fixer which detachably couples the measurement housing to the frame unit.

The measurement housing may be formed including a synthetic resin material.

The housing fixer may include a fixing-and-mounting part which is detachably coupled to the frame unit and a fixing-and-connecting part which is provided to be stretchable and connects the fixing-and-mounting part to the measurement housing.

The measurement housing unit may further include an image capturing unit protector which is mounted on the measurement housing, provided to surround the image capturing unit, and reduces a dose of radiation delivered to the image capturing unit so that damage to the image capturing unit is prevented.

The image capturing unit protector may be formed including at least one of acrylic and lead glass.

The scintillation unit may include a scintillation plate, which is mounted on the measurement housing unit and emits light due to the radiation exposed by the radiation exposure unit, and a scintillation cover part, which is disposed between the radiation exposure unit and the scintillation plate and, when the radiation is exposed by the radiation exposure unit, increases an amount of electrons transported toward the scintillation plate so that an amount of light emitted by the scintillation plate is increased.

The image capturing unit may capture the image of the scintillation unit while being disposed at an outer side of a path along which the radiation exposed by the radiation exposure unit passes through the scintillation unit.

The image capturing unit may be disposed to be tilted at a predetermined angle with respect to the scintillation unit, and the dose measuring unit may include an image input part which receives the captured image, an image corrector which corrects the captured image on the basis of a position or an angle of the image capturing unit, and a dose measuring member which measures, on the basis of a corrected image obtained by the image corrector, a dose of radiation to which the scintillation unit is exposed.

The corrected image may be generated by inversely inputting an image distortion rate, which is an extent to which a comparison image, which is obtained by placing a reference image at a position at which the scintillation unit is mounted and picking up the reference image using the image capturing unit, is distorted as compared with the reference image.

A method for measuring a radiation dose according to the present invention includes: a fixing operation in which a measurement housing unit is fixed to a frame unit at a position facing a radiation exposure unit; a radiation exposure operation in which a scintillation unit mounted on the measurement housing unit is exposed to radiation; an image capturing operation in which, by an image capturing unit mounted on the measurement housing unit, an image of the scintillation unit is captured to obtain a captured image; an image correcting operation in which, on the basis of a position and an angle of the image capturing unit, the captured image is corrected to obtain a corrected image; and a dose measuring operation in which, on the basis of the corrected image, a dose of radiation to which the scintillation unit is exposed is measured.

Advantageous Effects

According to a device and method for measuring a radiation dose according to the present invention, since an image of a scintillation unit can be captured without applying a reflective mirror or the like and a measurement housing unit is formed including synthetic resin such as the Foamex material, the volume and weight of the device can be reduced, and thus the device can be mounted on a moving frame or the like.

Also, since the measurement housing unit can be detachably coupled to the moving frame or the like, mounting and managing of the device are facilitated.

Also, since a captured image is corrected by a dose measuring unit, an in vivo radiation dose can be accurately analyzed from the captured image.

MODES OF THE INVENTION

Figure 1:
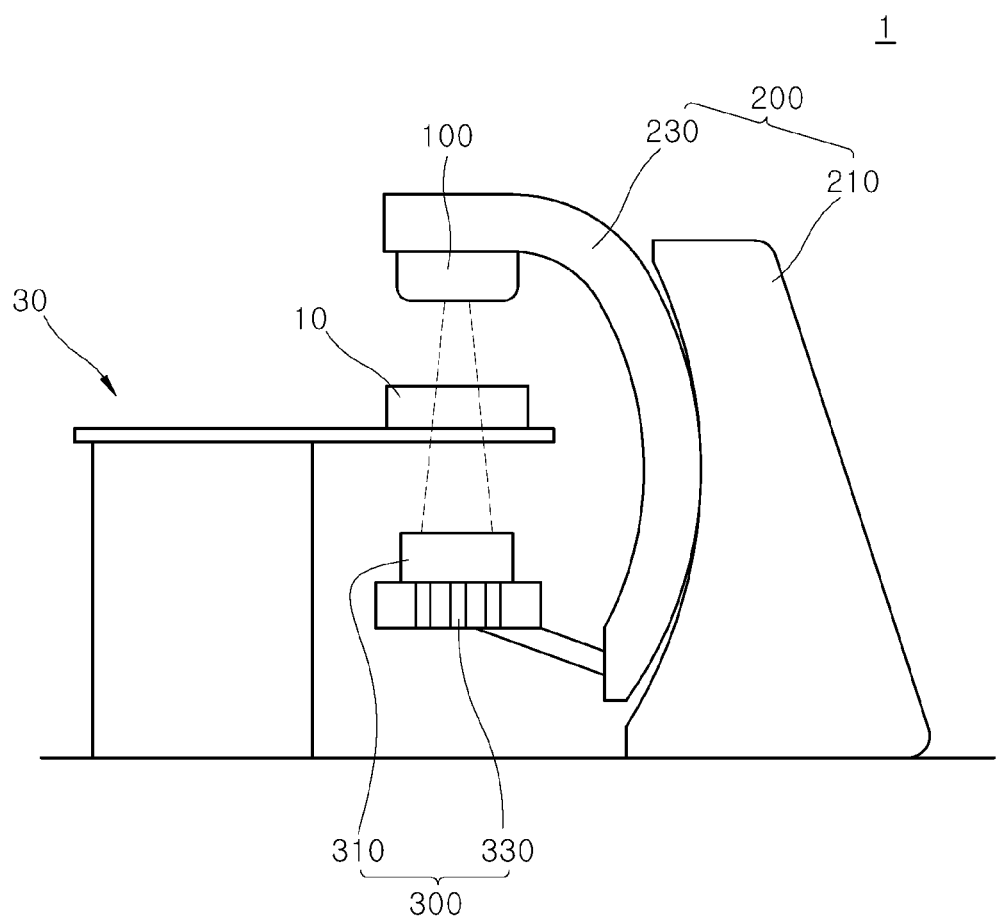
FIG. 1 is a schematic diagram illustrating a radiation dose measuring device according to an embodiment of the present invention.

Hereinafter, exemplary embodiments of a device and method for measuring a radiation dose according to the present invention will be described with reference to the accompanying drawings. In this process, the thicknesses of lines, the sizes of elements, or the like illustrated in the drawings may have been exaggerated for clarity and convenience of description.

Also, terms used herein are those defined in consideration of functions in the present invention, and the terms may be changed according to an intention or practice of a user or an operator. Therefore, such terms should be defined on the basis of the content throughout the present specification.

Figure 2:
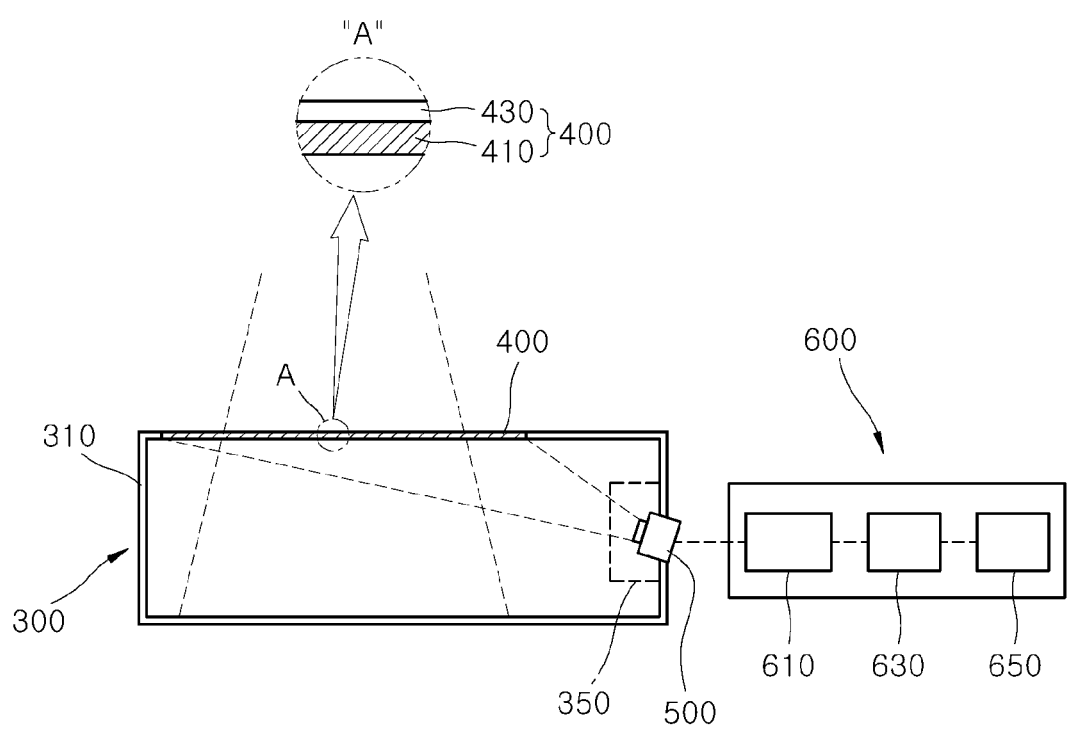
FIG. 2 is a cross-sectional view schematically illustrating a measurement housing unit, a scintillation unit, an image capturing unit, and a dose measuring unit according to an embodiment of the present invention.

FIG. 1 is a schematic diagram illustrating a radiation dose measuring device according to an embodiment of the present invention, and FIG. 2 is a cross-sectional view schematically illustrating a measurement housing unit, a scintillation unit, an image capturing unit, and a dose measuring unit according to an embodiment of the present invention.

Referring to FIGS. 1 and 2, a radiation dose measuring device 1 according to the present embodiment includes a radiation exposure unit 100, a frame unit 200, a measurement housing unit 300, a scintillation unit 400, an image capturing unit 500, and a dose measuring unit 600 and exposes a subject 10, e.g., a biological tissue, to radiation and measures a dose of radiation passing through the biological tissue in real time.

The radiation exposure unit 100 exposes the scintillation unit 400 to radiation. In the present embodiment, the radiation exposure unit 100 may be mounted on the frame unit 200 and emit X-rays, gamma rays, high-energy electrons, high-energy protons, or other high-energy particles.

Also, the radiation exposure unit 100 may include any one of an X-ray generating device, a radiation isotope source, or a linear accelerator or may receive and emit high-energy particle beam which is input from the outside of the radiation dose measuring device 1 and generated by acceleration by a particle accelerator or the like.

Of course various other methods may be applied to the radiation exposure unit 100 as long as the radiation exposure unit 100 can emit radiation.

The frame unit 200 supports the radiation exposure unit 100 and moves the radiation exposure unit 100. In the present embodiment, the frame unit 200 includes a fixing frame 210 and a moving frame 230. The fixing frame 210 is fixed to a floor surface, a ceiling, a wall, or the like to support the moving frame 230, the radiation exposure unit 100, and the like.

A substantially central portion of the moving frame 230 is rotatably coupled to the fixing frame 210, and the radiation exposure unit 100 and the measurement housing unit 300 are mounted on both end portions of the moving frame 230 so as to face each other. In this way, the radiation emitted from the radiation exposure unit 100 is delivered to the scintillation unit 400 mounted on the measurement housing unit 300.

A table 30 or the subject 10 is located between the both end portions of the moving frame 230, and the both end portions rotate about the table 30 or the subject 10.

Accordingly, regardless of the extent of rotation of the moving frame 230, the radiation emitted from the radiation exposure unit 100 passes through the table 30 or the subject 10 located on the table 30 and reaches the scintillation unit 400 mounted on the measurement housing unit 300.

Figure 3:
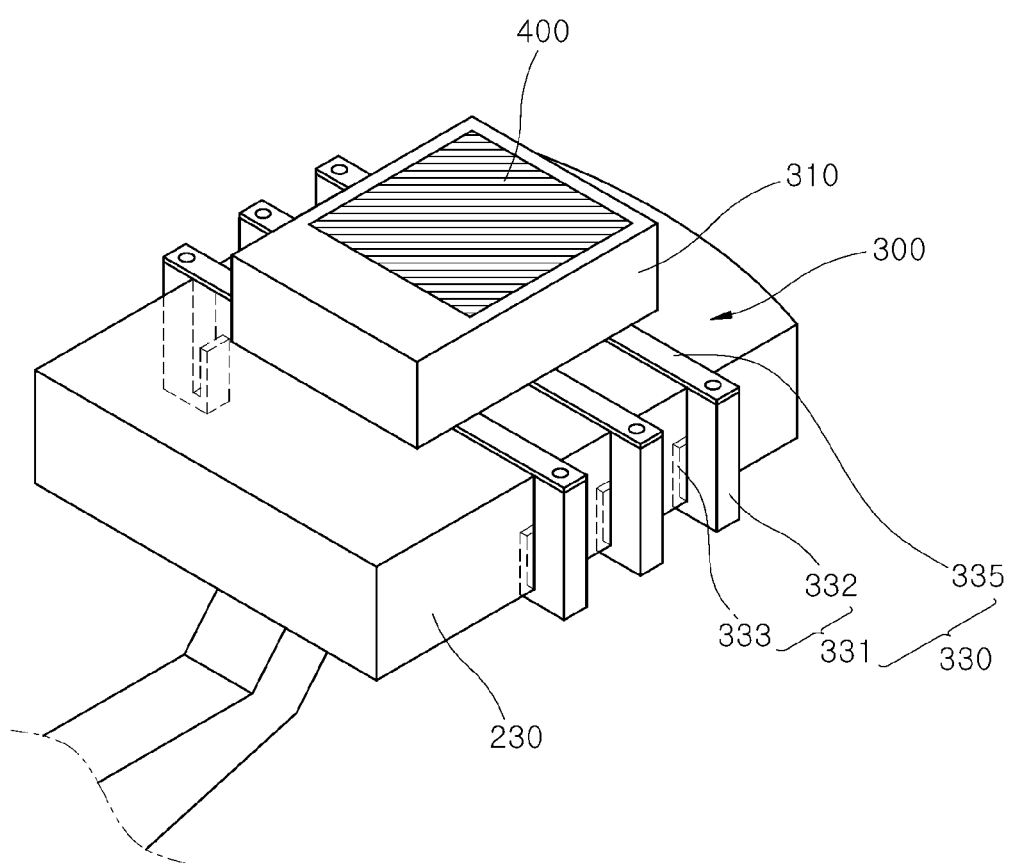
FIG. 3 is a perspective view illustrating a state in which the measurement housing unit is mounted on a moving frame according to an embodiment of the present invention.
Figure 4:
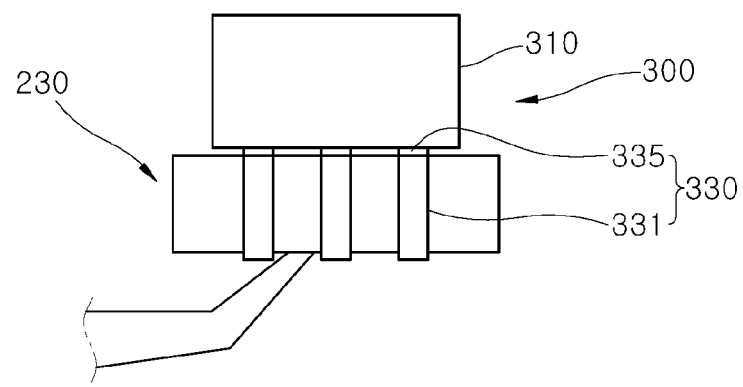
FIG. 4 is a front view illustrating the state in which the measurement housing unit is mounted on the moving frame according to an embodiment of the present invention.
Figure 5:
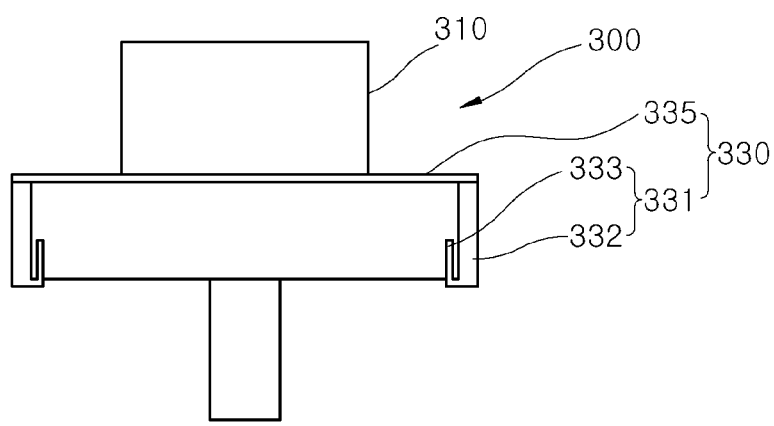
FIG. 5 is a side view illustrating the state in which the measurement housing unit is mounted on the moving frame according to an embodiment of the present invention.

FIG. 3 is a perspective view illustrating a state in which the measurement housing unit is mounted on a moving frame according to an embodiment of the present invention, FIG. 4 is a front view illustrating the state in which the measurement housing unit is mounted on the moving frame according to an embodiment of the present invention, and FIG. 5 is a side view illustrating the state in which the measurement housing unit is mounted on the moving frame according to an embodiment of the present invention.

Referring to FIGS. 3 to 5, the measurement housing unit 300 is mounted on the frame unit 200, specifically, the moving frame 230. In the present embodiment, the measurement housing unit 300 includes a measurement housing 310 and a housing fixer 330.

The measurement housing 310 is disposed to face the radiation exposure unit 100 and has the scintillation unit 400 and the image capturing unit 500 mounted thereon. In the present embodiment, the measurement housing 310 is formed including a synthetic resin material. Specifically, the measurement housing 310 is formed including the Foamex material whose specific gravity is about 0.65 to 0.85, that is formed by foaming polyvinyl chloride (PVC).

In the present embodiment, since the measurement housing 310 is formed including the synthetic resin material, especially, the Foamex material, the weight is reduced as compared with when a metallic material is applied, and it is possible to prevent the radiation, when the measurement housing 310 is exposed, from scattering due to the measurement housing 310.

In this way, since the weight of the measurement housing 310 is significantly reduced, as compared with when a metallic material is applied, while allowing the measurement housing 310 to stably support the scintillation unit 400, the image capturing unit 500, and the like, even when the measurement housing 310 is mounted on the moving frame 230, the moving frame 230 is prevented from being deformed, damaged, or malfunctioning due to the weight or the like of the measurement housing 310.

Also, in order to minimize an influence of outside light on a process in which the image capturing unit 500 picks up an image of the scintillation unit 400, an outer surface of the measurement housing 310 may be finished with black colored paper or the like.

Figure 6:
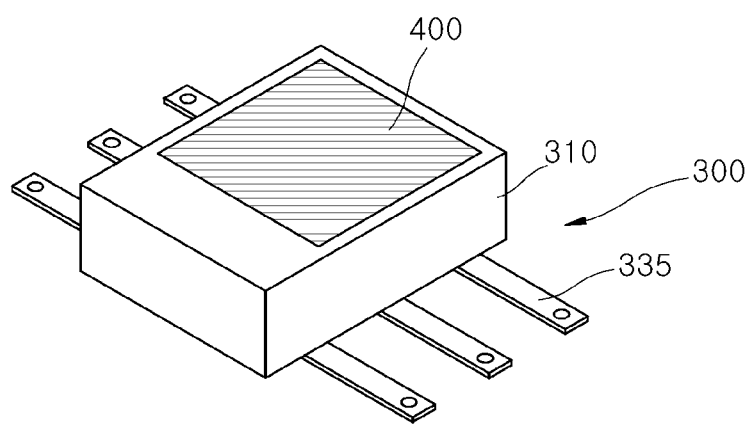
FIG. 6 is a view illustrating a state in which a fixing-and-connecting part is mounted on the measurement housing unit according to an embodiment of the present invention.
Figure 7:
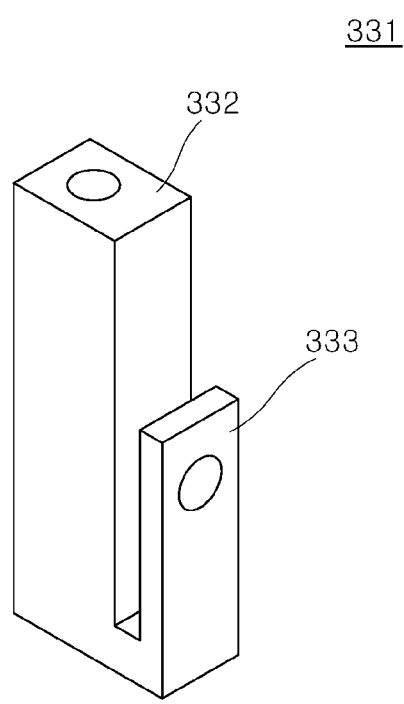
FIG. 7 is a view illustrating a fixing-and-mounting part according to an embodiment of the present invention.

FIG. 6 is a view illustrating a state in which a fixing-and-connecting part is mounted on the measurement housing unit according to an embodiment of the present invention, and FIG. 7 is a view illustrating a fixing-and-mounting part according to an embodiment of the present invention.

Referring to FIGS. 6 and 7, the housing fixer 330 detachably couples the measurement housing 310 to the frame unit 200, specifically, the moving frame 230. In the present embodiment, the housing fixer 330 includes a fixing-and-mounting part 331 and a fixing-and-connecting part 335.

The fixing-and-mounting part 331 is detachably coupled to the frame unit 200. In the present embodiment, a plurality of, e.g., three pairs of, fixing-and-mounting parts 331 are provided and detachably coupled to the frame unit 200, specifically, the moving frame 230, by methods such as fitting and screwing.

In the present embodiment, the fixing-and-mounting part 331 includes a fixing-and-mounting body 332 and a fixing-and-mounting catcher 333. The fixing-and-mounting body 332 is coupled to the fixing-and-connecting part 335 by methods such as bolting and fitting and comes in contact with a side surface or the like of the moving frame 230.

The fixing-and-mounting catcher 333 is connected to the fixing-and-mounting body 332 and inserted into a groove portion (not illustrated) or the like concavely formed in the moving frame 230 so that the fixing-and-mounting catcher 333 is fixed to the moving frame 230.

The fixing-and-mounting part 331 may be formed in various shapes corresponding to the shape of the moving frame 230 on which the fixing-and-mounting part 331 is to be mounted. Other than being detachably coupled to the moving frame 230, the fixing-and-mounting part 331 may come in close contact with the moving frame 230 by having both end portions connected to the fixing-and-connecting part 335 having stretchability.

The fixing-and-connecting part 335 is provided to be stretchable and connects the fixing-and-mounting part 331 to the measurement housing 310. In the present embodiment, the fixing-and-connecting part 335 is formed as a belt made of a stretchable material or formed including the Foamex material. The fixing-and-connecting part 335 is connected to the fixing-and-mounting part 331 coupled to the moving frame 230 and fixes the measurement housing 310 in close contact with the moving frame 230.

In the present embodiment, the measurement housing unit 300 further includes an image capturing unit protector 350 (see FIG. 2). The image capturing unit protector 350 is mounted on the measurement housing 310 and provided to surround the image capturing unit 500 to reduce a dose of radiation delivered to the image capturing unit 500 so that damage to the image capturing unit 500 is prevented.

In the present embodiment, the image capturing unit protector 350 is formed including at least one of acrylic and lead glass so that visible light is transmitted through the image capturing unit protector 350 and transferred to the image capturing unit 500 while radiation is blocked by the image capturing unit protector 350. In this way, a sensor or the like of the image capturing unit 500 is prevented from being damaged due to the radiation reflected and scattered from the scintillation unit 400 or the like.

Figure 8:
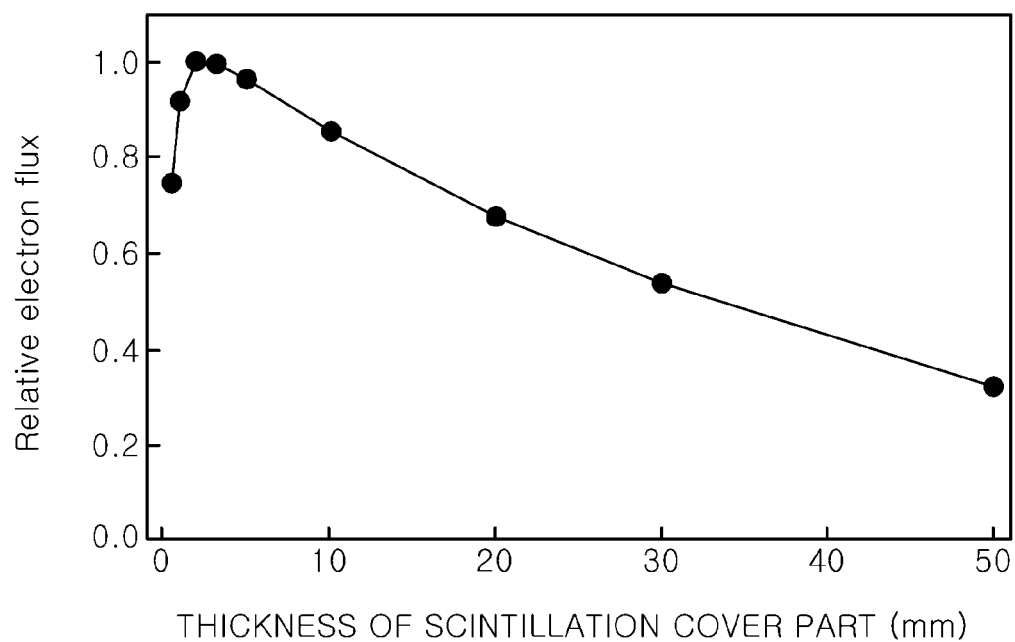
FIG. 8 is a graph showing, in a scintillation cover part, an amount of electrons transported to a scintillation plate according to a change in a thickness of the scintillation cover part according to an embodiment of the present invention.

FIG. 8 is a graph showing, in a scintillation cover part, an amount of electrons transported to a scintillation plate according to a change in a thickness of the scintillation cover part according to an embodiment of the present invention. Referring to FIGS. 2 and 8, the scintillation unit 400 is mounted on the measurement housing unit 300 and emits light due to be excited by the radiation exposed by the radiation exposure unit 100. In the present embodiment, the scintillation unit 400 is formed in the shape of a substantially rectangular plate and mounted on an upper side surface of the measurement housing unit 300. In the present embodiment, the scintillation unit 400 includes a scintillation plate 410 and a scintillation cover part 430.

The scintillation plate 410 is detachably mounted on the measurement housing unit 300 and emits light due to the radiation exposed by the radiation exposure unit 100. The scintillation cover part 430 is disposed between the radiation exposure unit 100 and the scintillation plate 410 and, in response to the radiation from the radiation exposure unit 100, increases the amount of electrons transported toward the scintillation plate 410, thereby increasing the extent to which the scintillation plate 410 emits light.

In the present embodiment, the scintillation cover part 430 is formed including materials with relatively large atomic numbers, such as copper, brass, and steel, and formed in in a substantially plate-like shape. The scintillation cover part 430 is disposed at an upper side surface of the scintillation plate 410.

Referring to FIG. 8, it can be seen that the amount of electrons transported to the scintillation plate 410 changes according to the thickness of the scintillation cover part 430. The scintillation cover part 430 may be formed in a thickness that causes the amount of electrons to be increased as compared with when the scintillation cover part 430 is not mounted. In this way, the amount of electrons transported to the scintillation plate 410 may be increased.

In the present embodiment, the scintillation cover part 430 is formed including copper and formed in a thickness of 1.00 to 2.25 mm so that an increase in the overall weight of the scintillation unit 400 is limited while the amount of electrons transported to the scintillation plate 410 is increased.

The image capturing unit 500 picks up an image of the scintillation unit 400. In the present embodiment, the image capturing unit 500 captures the image of the scintillation unit 400 while being disposed at an outer side of a path along which the radiation exposed by the radiation exposure unit 100 passes through the scintillation unit 400.

In the present embodiment, the image capturing unit 500 captures the image of the scintillation unit 400 while being disposed at an outer side of a path along which the radiation exposed by the radiation exposure unit 100 passes through the scintillation unit 400. In this way, by preventing the radiation passing through the scintillation unit 400 from being directly delivered to the image capturing unit 500, damage to the image capturing unit 500 is prevented.

In the present embodiment, the image capturing unit 500 captures an image of the scintillation unit 400 while being disposed to be tilted at a predetermined angle with respect to the scintillation unit 400. The image capturing unit 500 may include a wide-angle lens and capture an image of the scintillation unit 400 while being disposed in the vicinity of the scintillation unit 400. In this way, it is possible to reduce the size and volume of the measurement housing 310 forming a darkroom.

A captured image 40 obtained by the image capturing unit 500 is transmitted to the dose measuring unit 600. Since, as described above, the image capturing unit 500 is mounted on the measurement housing 310 fixed to the moving frame 230, the image capturing unit 500 is wirelessly connected to the dose measuring unit 600 to prevent entangling of wires or interference with another device when the moving frame 230 rotates.

In the present embodiment, the image capturing unit 500 may be a small camera such as a mirrorless camera and an action camera. The image capturing unit 500 is detachably mounted on the measurement housing unit 300 and wirelessly connected to the dose measuring unit 600.

Figure 9:
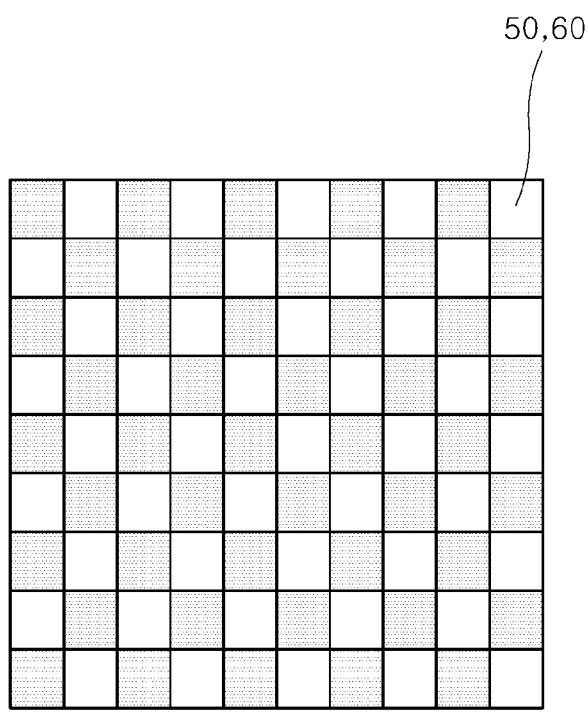
FIG. 9 is a view illustrating a reference image according to an embodiment of the present invention.
Figure 10:
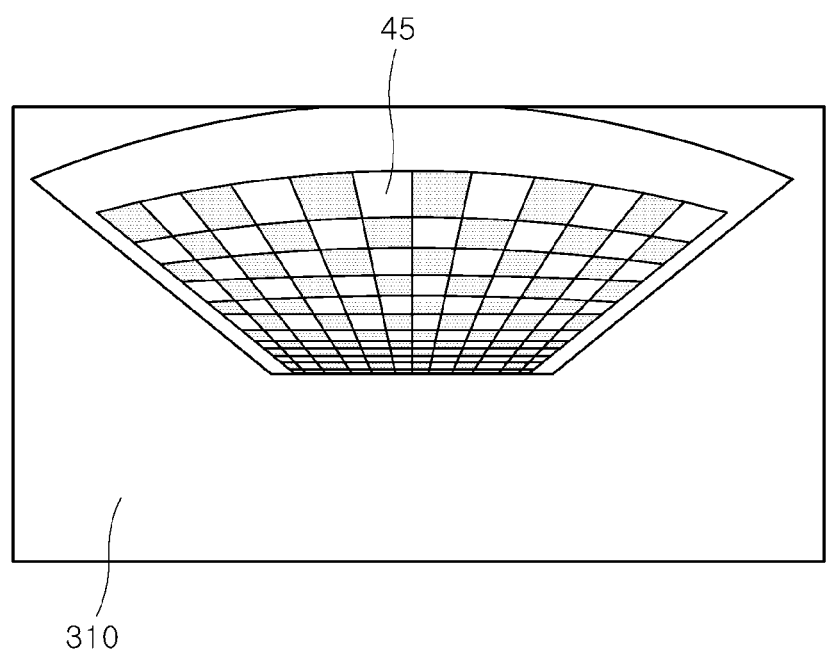
FIG. 10 is a view illustrating a comparison image according to an embodiment of the present invention.
Figure 11:
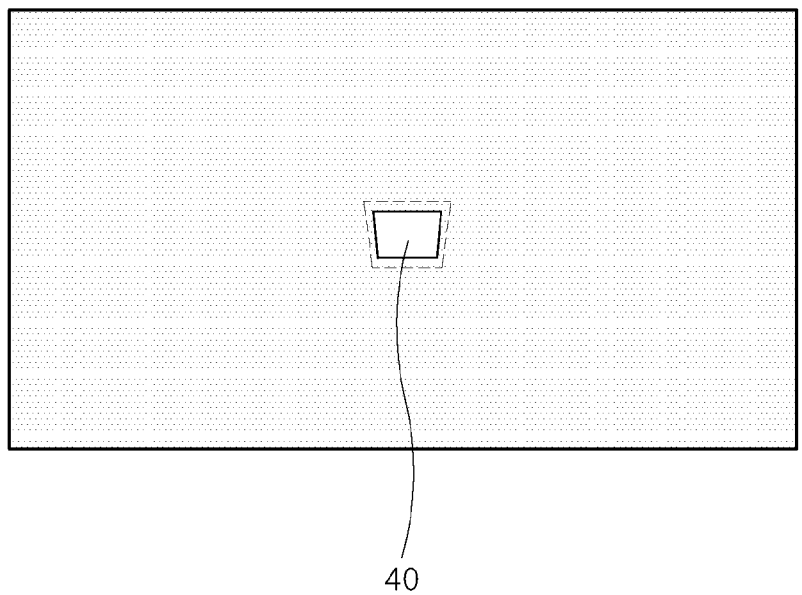
FIG. 11 is a view illustrating a captured image according to an embodiment of the present invention.
Figure 12:
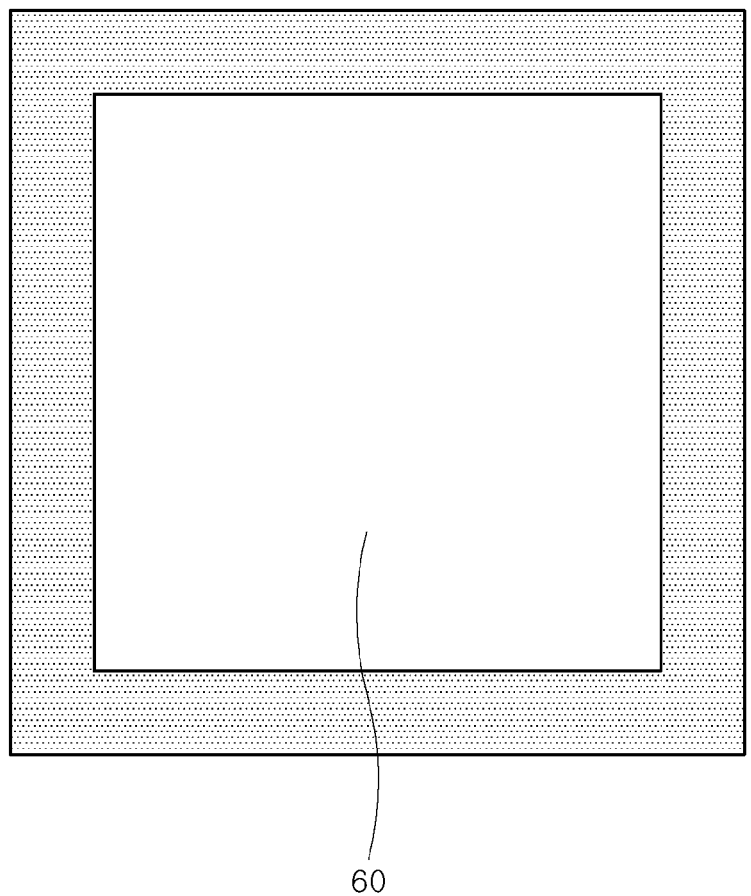
FIG. 12 is a view illustrating a corrected image according to an embodiment of the present invention.

FIG. 9 is a view illustrating a reference image according to an embodiment of the present invention, FIG. 10 is a view illustrating a comparison image according to an embodiment of the present invention, FIG. 11 is a view illustrating a captured image according to an embodiment of the present invention, and FIG. 12 is a view illustrating a corrected image according to an embodiment of the present invention.

Referring to FIGS. 9 to 12, the dose measuring unit 600 measures, on the basis of the captured image 40 obtained by the image capturing unit 500, a dose of radiation to which the scintillation unit 400 is exposed. In the present embodiment, the dose measuring unit 600 includes a captured image input part 610, an image corrector 630, and a dose measuring member 650.

The captured image input part 610 receives the captured image 40 from the image capturing unit 500. As described above, the captured image input part 610 may be wirelessly connected to the image capturing unit 500. The captured image input part 610 receives the captured image 40 from the image capturing unit 500 in real time.

The image corrector 630 corrects the captured image 40 on the basis of a position or an angle of the image capturing unit 500 and generates a corrected image 60. In the present embodiment, the corrected image 60 is generated by inversely inputting an image distortion rate, which is an extent to which a comparison image 45, which is obtained by placing a reference image 50 at a position at which the scintillation unit 400 is mounted and picking up the reference image 50 using the image capturing unit 500, is distorted as compared with the reference image 50, to the captured image 40.

The dose measuring member 650 analyzes the corrected image 60 obtained by the image corrector 640 and measures a dose of radiation to which the scintillation unit 400 is exposed. In the present embodiment, the image corrector 630 may measure a dose of radiation that reached the scintillation unit 400 by using a method of measuring a brightness or the like for each point in the corrected image 60.

Figure 13:
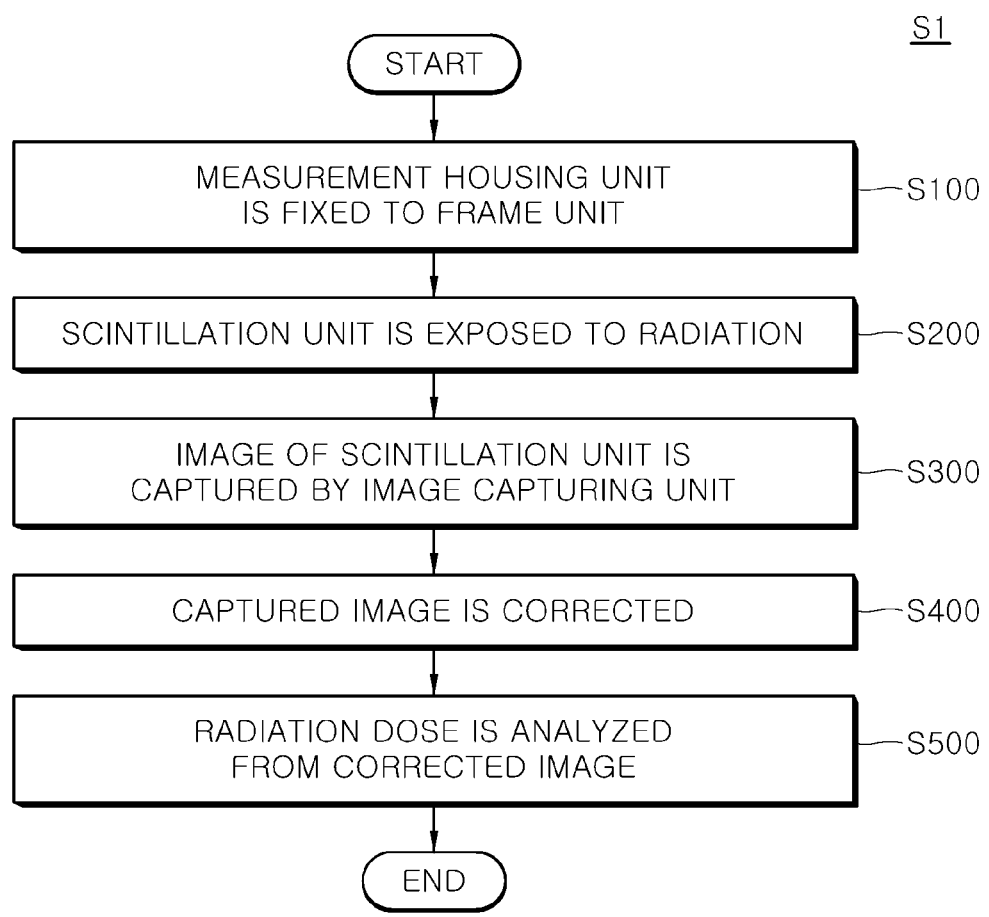
FIG. 13 is a flowchart illustrating a method of measuring a radiation dose according to an embodiment of the present invention.

FIG. 13 is a flowchart illustrating a method of measuring a radiation dose according to an embodiment of the present invention. A method S1 for measuring a radiation dose according to an embodiment of the present invention and advantageous effects thereby will be described below with reference to FIG. 13.

The method S1 for measuring a radiation dose according to the present embodiment includes a fixing operation S100, a radiation exposure operation S200, an image capturing operation S300, an image correcting operation S400, and a dose measuring operation S500.

In the fixing operation S100, a measurement housing unit 300 is fixed to a frame unit 200 at a position corresponding to a radiation exposure unit 100. The measurement housing unit 300 includes a fixing-and-mounting part 331 and a fixing-and-connecting part 335 and is detachably coupled to a moving frame 230.

In the radiation exposure operation S200, a scintillation unit 400 mounted on the measurement housing unit 300 is exposed to radiation. In the present embodiment, in the radiation exposure operation S200, radiation is exposed by the radiation exposure unit 100 which is disposed to face the measurement housing unit 300 and mounted on the moving frame 230.

In the image capturing operation S300, by an image capturing unit 500 mounted on the measurement housing unit 300, an image of a scintillation unit 400 is captured to obtain a captured image 40.

In the image correcting operation S400, on the basis of a position and an angle of the image capturing unit 500, the captured image 40 is corrected to obtain a corrected image 60. In the image correcting operation S500 according to the present embodiment, the corrected image 60 is generated by inversely inputting an image distortion rate, which is an extent to which a comparison image 45, which is obtained by placing a reference image 50 at a position at which the scintillation unit 400 is mounted and picking up the reference image 50 using the image capturing unit 500, is distorted as compared with the reference image 50, to the captured image 40.

In the dose measuring operation S500, on the basis of the corrected image 60, a dose of radiation to which the scintillation unit 400 is exposed is measured.

As a result of gamma analysis for comparing a result of the actual EBT3 film measurement and a result of measuring a radiation dose using the radiation dose measuring device 1 according to the present embodiment, the results matched by 94.24% in a 3%/3 mm condition, 98.73% in a 4%/4 mm condition, and 100.00% in a 5%/5 mm condition. Therefore, it can be seen that the radiation dose measuring device 1 according to the present embodiment has very high accuracy.

In this way, according to the radiation dose measuring device 1 and the measurement method S1 of the present embodiment, since an image of the scintillation unit 400 may be captured without applying a reflective mirror or the like, and the measurement housing unit 300 is formed including the Foamex material, the volume and weight of the device may be reduced.

Also, according to the radiation dose measuring device 1 and the measurement method S1 of the present embodiment, by correcting distortion of the captured image 40 by the dose measuring unit 600, it is possible to accurately analyze an in vivo radiation dose from the captured image 40.

The present invention has been described by referring to the embodiments illustrated in the accompanying drawings, but the above description is merely illustrative, and those of ordinary skill in the art to which the present invention pertains should understand that various modifications and other equivalent embodiments are possible from the above embodiments. Therefore, the technical scope of the present invention should be defined by the claims below.

The invention claimed is:

1. A device for measuring a radiation dose, comprising:
a radiation exposure unit comprising any one of X-ray generator, a radiation isotope source or a linear accelerator configured to emit radiation;
a frame unit comprising a fixing frame and a moving frame rotatably coupled to the fixing frame, the moving frame being configured to support the radiation exposure unit at one end portion of the moving frame of the frame unit;
a measurement housing unit mounted on the other end portion of the moving frame of the frame unit;
a scintillation unit mounted on the measurement housing unit and comprising a scintillation cover part and a scintillation plate configured to emit light in response to the radiation emitted by the radiation exposure unit;
an image capturing unit comprising a camera configured to capture an image of the scintillation unit; and
a dose measuring unit comprising an image corrector configured to correct distortion of the captured image to measure, on the basis of a position and an angle of the image capturing unit, a dose of radiation to which the scintillation unit is exposed.

2. The device of claim 1, wherein the measurement housing unit includes:
a measurement housing on which the scintillation unit and the image capturing unit are mounted; and
a housing fixer configured to detachably couple the measurement housing to the frame unit.

3. The device of claim 2, wherein the measurement housing is formed including a synthetic resin material.

4. The device of claim 2, wherein the measurement housing unit further includes an image capturing unit protector which is mounted on the measurement housing, provided to surround the image capturing unit, and reduces a dose of radiation delivered to the image capturing unit so that damage to the image capturing unit is prevented.

5. The device of claim 4, wherein the image capturing unit protector is formed including at least one of acrylic and lead glass.

6. The device of claim 1, wherein the scintillation cover part is disposed between the radiation exposure unit and the scintillation plate, and is configured to, when the radiation is emitted by the radiation exposure unit, increase an amount of electrons transported toward the scintillation plate so that an amount of light emitted by the scintillation plate is increased.

7. The device of claim 1, wherein the image capturing unit comprising the camera captures the image of the scintillation unit while being disposed at an outer side of a path along which the radiation emitted by the radiation exposure unit passes through the scintillation unit.

8. The device of claim 7, wherein:
the image capturing unit is disposed to be tilted at a predetermined angle with respect to the scintillation unit; and
the dose measuring unit includes:
a captured image input part which receives the captured image, and
a dose measuring member which measures, on the basis of a corrected image obtained by the image corrector, a dose of radiation to which the scintillation unit is exposed.

9. The device of claim 8, wherein the corrected image is generated by inversely inputting an image distortion rate, which is an extent to which a comparison image, which is obtained by placing a reference image at a position at which the scintillation unit is mounted and picking up the reference image using the image capturing unit, is distorted as compared with the reference image, to the captured image to correct the distortion of the captured image and obtain the corrected image.

10. The device of claim 1, wherein the measurement housing unit is detachably coupled to the moving frame.

11. A device for measuring a radiation dose, comprising:
a radiation exposure unit comprising any one of X-ray generator, a radiation isotope source or a linear accelerator configured to emit radiation;
a frame unit comprising a fixing frame and a moving frame configured to support the radiation exposure unit;
a measurement housing unit mounted on the frame unit;
a scintillation unit mounted on the measurement housing unit and comprising a scintillation cover part and a scintillation plate configured to emit light in response to the radiation emitted by the radiation exposure unit;
an image capturing unit comprising a camera configured to capture an image of the scintillation unit; and
a dose measuring unit comprising an image corrector configured to correct distortion of the captured image to measure, on the basis of a position and an angle of the image capturing unit, a dose of radiation to which the scintillation unit is exposed,
wherein the measurement housing unit includes:
a measurement housing on which the scintillation unit and the image capturing unit are mounted; and
a housing fixer configured to detachably couple the measurement housing to the frame unit, and
wherein the housing fixer includes:
a fixing-and-mounting part detachably coupled to the frame unit; and
a fixing-and-connecting part provided to be stretchable and connect the fixing-and-mounting part to the measurement housing.

12. A method for measuring a radiation dose, the method comprising:
performing a fixing operation in which a measurement housing unit is fixed to a frame unit at a position facing a radiation exposure unit, the frame unit comprising a fixing frame and a moving frame which is rotatably coupled to the fixing frame, and the moving frame being configured to support the radiation exposure unit at one end portion and support the measurement housing unit at the other end portion of the frame unit;
performing a radiation exposure operation in which a scintillation unit mounted on the measurement housing unit is exposed to radiation;

performing an image capturing operation in which, by an image capturing unit comprising a camera mounted on the measurement housing unit, an image of the scintillation unit is captured to obtain a captured image;

performing an image correcting operation in which, on the basis of a position and an angle of the image capturing unit, distortion of the captured image is corrected to obtain a corrected image; and performing a dose measuring operation in which, on the basis of the corrected image, a dose of radiation to which the scintillation unit is exposed is measured.

13. The method of claim 12, wherein the performing of the image correcting operation further comprises:

inversely inputting an image distortion rate, which is an extent to which a comparison image, which is obtained by placing a reference image at a position at which the scintillation unit is mounted and picking up the reference image using the image capturing unit, is distorted as compared with the reference image, to the captured image to correct the distortion of the captured image and obtain the corrected image.

14. The method of claim 12, wherein the measurement housing unit is detachably coupled to the moving frame.

* * * * *